United States Patent
Piccagli

(10) Patent No.: US 10,441,299 B2
(45) Date of Patent: Oct. 15, 2019

(54) CATHETER WITH DEFLECTABLE TIP

(71) Applicant: Invatec S.p.A., Roncadelle (IT)

(72) Inventor: Francesco Piccagli, Roncadelle (IT)

(73) Assignee: Invatec S.P.A., Roncadelle (IT)

( * ) Notice: Subject to any disclaimer, the term of this patent is extended or adjusted under 35 U.S.C. 154(b) by 433 days.

(21) Appl. No.: 15/193,190

(22) Filed: Jun. 27, 2016

(65) Prior Publication Data

US 2016/0374701 A1 Dec. 29, 2016

Related U.S. Application Data

(63) Continuation of application No. 13/753,968, filed on Jan. 30, 2013, now Pat. No. 9,398,921.

(51) Int. Cl.
*A61M 25/01* (2006.01)
*A61B 17/22* (2006.01)
(Continued)

(52) U.S. Cl.
CPC .............. *A61B 17/22* (2013.01); *A61B 17/32* (2013.01); *A61B 17/320725* (2013.01); *A61B 90/39* (2016.02); *A61M 25/0074* (2013.01); *A61M 25/0155* (2013.01); *A61M 25/1002* (2013.01); *A61B 2017/00876* (2013.01);
(Continued)

(58) Field of Classification Search
CPC ........ A61B 17/3207; A61B 17/320725; A61B 2017/22051; A61B 2017/22071; A61B 2017/00318; A61M 25/10; A61M 25/104; A61M 25/0155; A61M 25/1002; A61M 2025/1056; A61M 2025/1068; A61M 2025/0058; A61M 2025/1043–1047; A61M 2025/1061; A61M 2025/1065; A61M 2025/1079; A61M 2025/1093; A61M 2025/0177; A61M 2025/0293; A61M 2025/0161
See application file for complete search history.

(56) References Cited

U.S. PATENT DOCUMENTS 5,002,532 A 3/1991 Gaiser et al.
5,460,608 A 10/1995 Loding et al.
(Continued)

FOREIGN PATENT DOCUMENTS

WO WO2007/033052 3/2007
WO WO2008/073126 6/2008
(Continued)

OTHER PUBLICATIONS

PCT/US2014/011140, PCT Search Report and Written Opinion, dated May 8, 2014.

*Primary Examiner* — Jonathan A Hollm

(57) ABSTRACT

A catheter having a distal balloon and a deformable guidewire shaft of the catheter. The deformable guidewire shaft is adjacent to and external to the balloon. Inflation of the balloon bends the deformable guidewire shaft in order to orient or deflect a distal tip of the deformable guidewire shaft in a desired direction to guide and direct a guidewire extending through the deformable guidewire shaft towards a specific endovascular region. For example, it may be desired to orient the distal tip of the guidewire shaft towards a target vessel of a bifurcation or the balloon catheter may be used to bypass a Chronic Total Occlusion (CTO).

12 Claims, 9 Drawing Sheets

(51) Int. Cl.
   *A61B 17/3207*  (2006.01)
   *A61M 25/00*    (2006.01)
   *A61M 25/10*    (2013.01)
   *A61B 90/00*    (2016.01)
   *A61B 17/32*    (2006.01)
   *A61B 17/00*    (2006.01)

(52) U.S. Cl.
   CPC ............ *A61B 2017/22045* (2013.01); *A61B 2017/22061* (2013.01); *A61B 2017/22095* (2013.01); *A61B 2017/320048* (2013.01); *A61B 2090/3966* (2016.02); *A61M 2025/0161* (2013.01)

(56) References Cited

U.S. PATENT DOCUMENTS

| | | |
|---|---|---|
| 5,569,184 A | 10/1996 | Crocker et al. |
| 5,667,493 A | 9/1997 | Janacek |
| RE36,104 E | 2/1999 | Solar |
| 6,068,610 A | 5/2000 | Ellis et al. |
| 6,221,080 B1 * | 4/2001 | Power ............... A61F 2/88 606/108 |
| 6,261,260 B1 | 7/2001 | Maki et al. |
| 6,514,228 B1 | 2/2003 | Hamilton et al. |
| 6,544,230 B1 | 4/2003 | Flaherty et al. |
| 7,729,738 B2 | 6/2010 | Flaherty et al. |
| 7,879,004 B2 | 2/2011 | Seibel et al. |
| 7,938,819 B2 | 5/2011 | Kugler et al. |
| 8,109,903 B2 | 2/2012 | Terliuc et al. |
| 2003/0125761 A1 | 7/2003 | Meens et al. |
| 2003/0163154 A1 | 8/2003 | Miyata et al. |
| 2003/0191436 A1 | 10/2003 | Horvers |
| 2008/0086191 A1 | 4/2008 | Valencia et al. |
| 2008/0147000 A1 | 6/2008 | Seibel et al. |
| 2010/0010522 A1 | 1/2010 | Shturman |
| 2010/0168665 A1 | 7/2010 | Skerven |
| 2011/0144677 A1 | 6/2011 | Ward et al. |

FOREIGN PATENT DOCUMENTS

| | | |
|---|---|---|
| WO | WO2008/120209 | 10/2008 |
| WO | WO2010/044816 | 4/2010 |

* cited by examiner

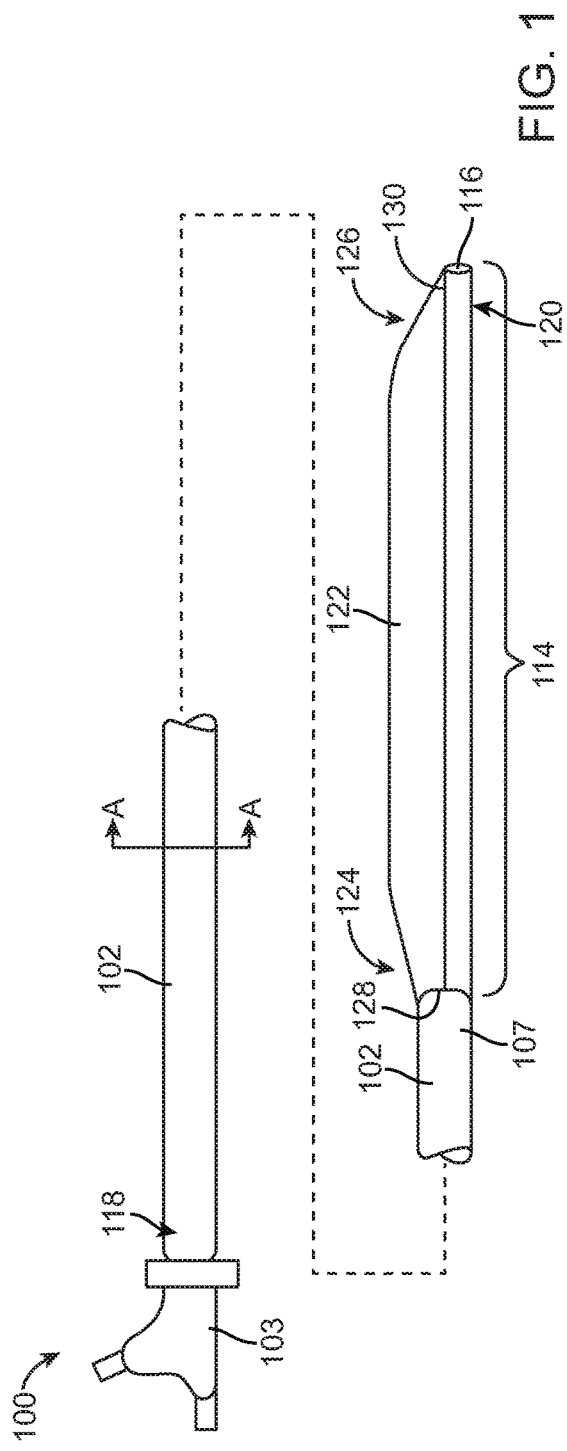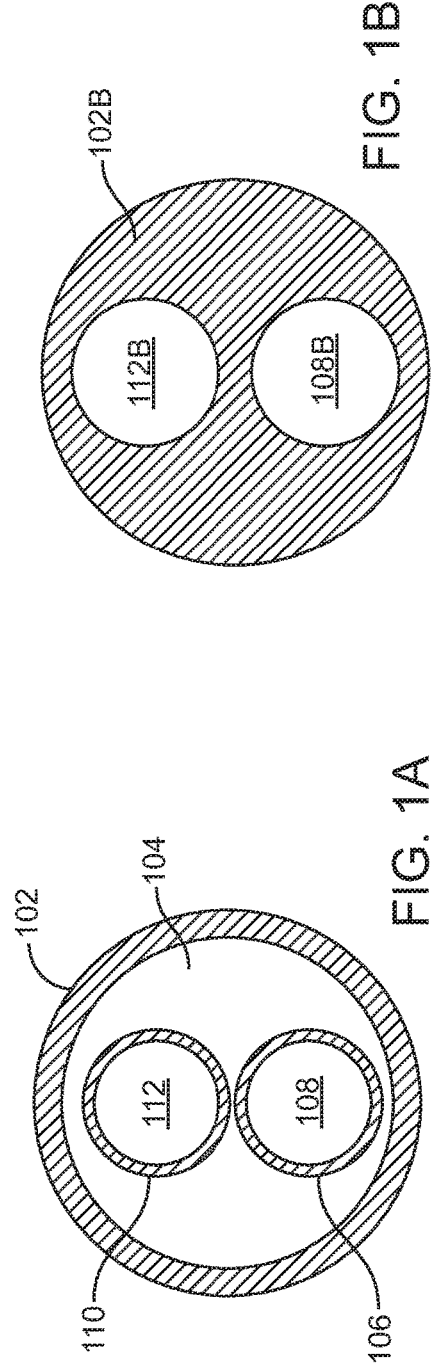

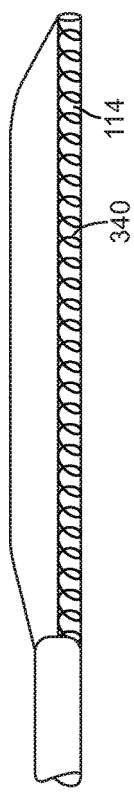
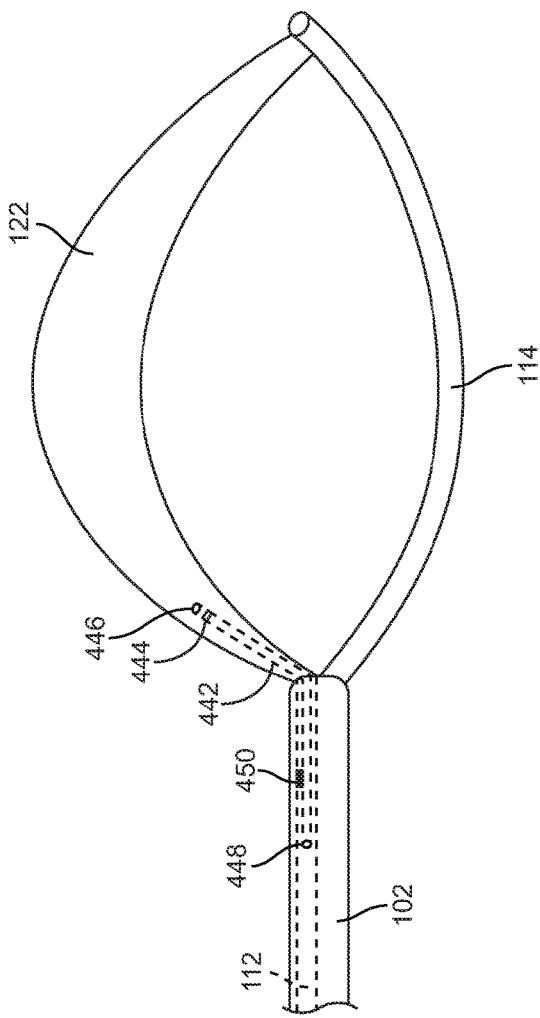

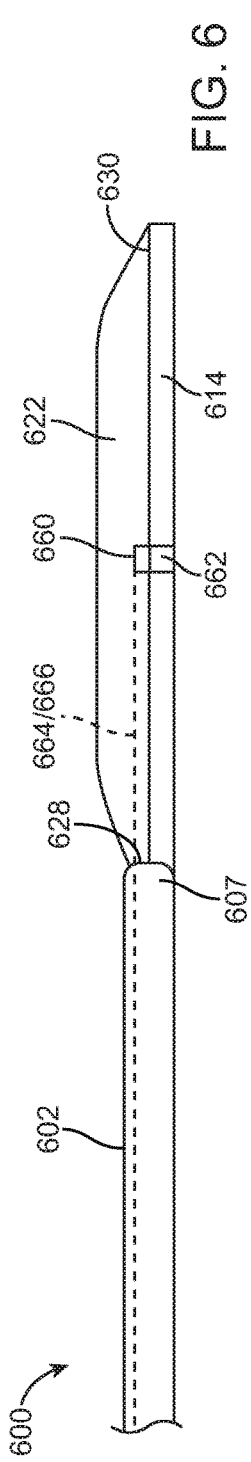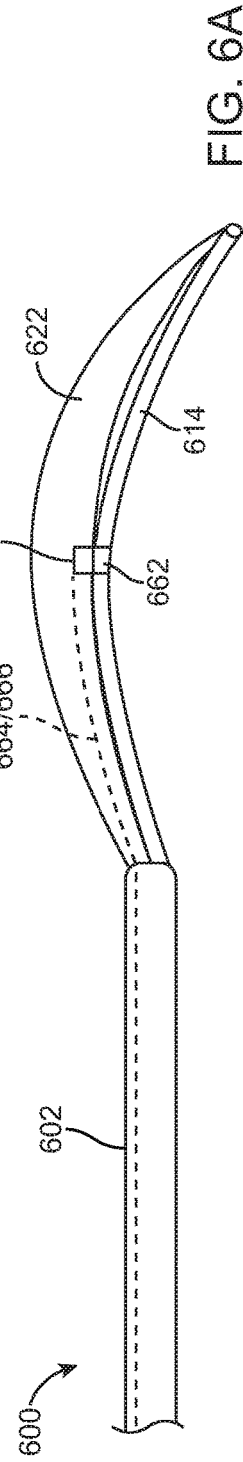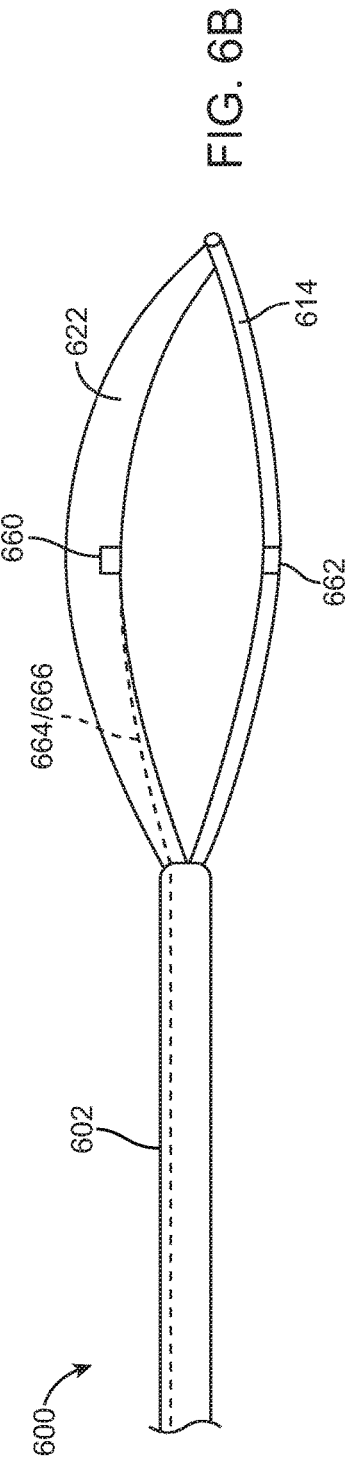

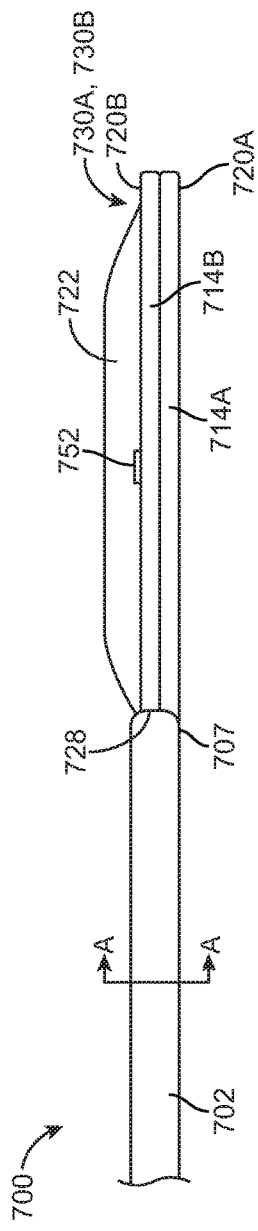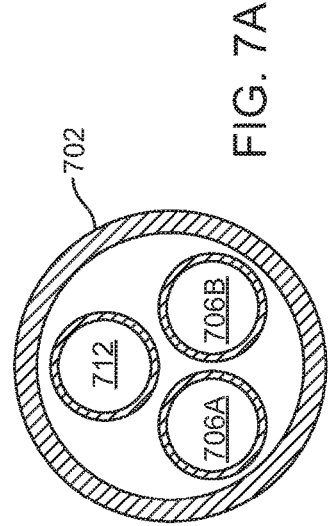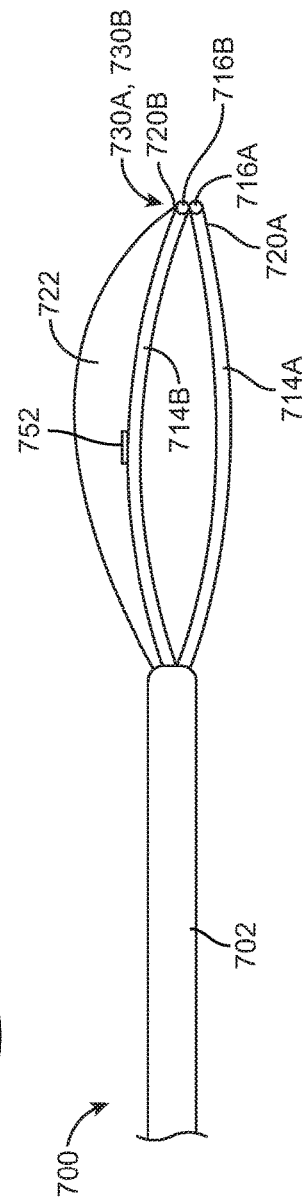

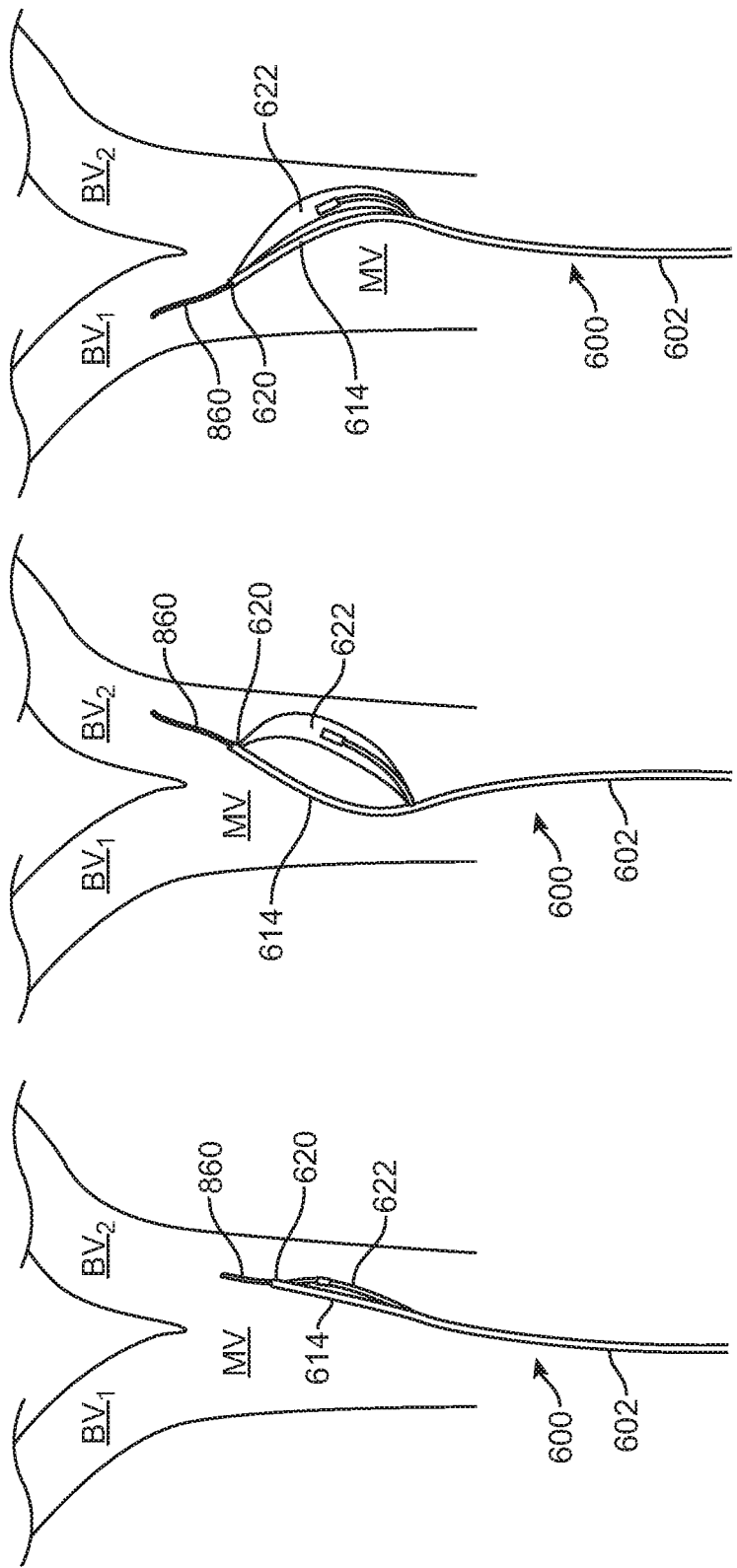

CATHETER WITH DEFLECTABLE TIP

RELATED APPLICATIONS

This application is a Continuation of and claims the benefit of U.S. patent application Ser. No. 13/753,968, filed Jan. 30, 2013, now allowed. The disclosures of which are herein incorporated by reference in their entirety.

FIELD OF THE INVENTION

The invention relates in general to catheters and in particular to a balloon catheter having a deflectable distal end.

BACKGROUND OF THE INVENTION

A variety of catheters for delivering a therapy and/or monitoring a physiological condition have been implanted or proposed for implantation in patients. Catheters may deliver therapy to, and/or monitor conditions associated with, the heart, muscle, nerve, brain, stomach or other organs or tissue. Many catheters are tracked through the vasculature to locate a therapeutic or diagnostic portion of the catheter at a target site. Such catheters must have flexibility to navigate the twists and turns of the vasculature, sufficient stiffness in the proximal portion thereof to be pushed through the vasculature alone or over a guidewire or through a lumen, and the capability of orienting a distal portion thereof in alignment with an anatomical feature at the target site so that a diagnostic or therapeutic procedure can be completed. In general terms, the catheter body must also resist kinking and be capable of being advanced through access pathways that twist and turn, sometimes abruptly at acute angles.

The distal portions of catheters frequently need to be selectively deflected or bent and straightened again while being advanced within the patient to steer the catheter distal end into a desired body lumen or chamber. For example, it may be necessary to direct the catheter distal end through tortuous anatomies and/or into a branch of vessel bifurcation. In addition, some procedures require high accuracy in guidewire orientation. For example, when a subintimal approach is selected for crossing a Chronic Total Occlusion (CTO), a guidewire needs to be accurately oriented to re-enter the true vessel lumen downstream of the CTO. Various steerable mechanisms have been disclosed to steer catheters and other elongated medical devices, e.g., steerable guidewires and stylets, and often involve the use of a deflection mechanism extending through a lumen of the catheter body to an attachment point in the catheter distal portion. For example, a deflection mechanism may include elongated wires referred to as control or pull wires, extending between a proximal control mechanism and the distal attachment point. More complex steerable catheters have two or more lumens and control wires extending from the handle to different points along the length or about the circumference of the catheter body to induce bends in multiple segments of the catheter body and/or in different directions.

Embodiments hereof are directed to a catheter having deflectable tip for navigating through or within a patient's anatomy.

BRIEF SUMMARY OF THE INVENTION

Embodiments hereof are directed to a balloon catheter including a main catheter shaft, a deformable guidewire shaft, and a balloon. The main catheter shaft includes a guidewire lumen and an inflation lumen. The deformable guidewire shaft extends from a distal end of the main catheter shaft, adjacent and external to the balloon, and the deformable guidewire shaft defines a lumen in fluid communication with the guidewire lumen of the main catheter shaft. The balloon extends from a distal end of the main catheter shaft and the inflation lumen of the main catheter shaft is in fluid communication with an interior of the balloon. A proximal bond fixes a proximal end of the balloon to a distal end of the main catheter shaft and a distal bond fixes a distal end of the balloon to a distal end of the deformable guidewire shaft, wherein an outer surface of the deformable guidewire shaft between the proximal bond and the distal bond is not bonded to the balloon. Balloon inflation causes the balloon and the deformable guidewire shaft to bend in radially opposing directions, thereby orienting the distal end of the deformable guidewire shaft in a direction different from that of the main catheter shaft.

Embodiments hereof are also related to a method of orienting a distal end of a balloon catheter in situ. The balloon catheter includes a main catheter shaft, a deformable guidewire shaft extending from a distal end of the main catheter shaft, and a balloon extending from a distal end of the main catheter shaft. The deformable guidewire shaft is adjacent and external to the balloon. A proximal bond fixes a proximal end of the balloon to a distal end of the main catheter shaft, a distal bond fixes a distal end of the balloon to a distal end of the deformable guidewire shaft, and an outer surface of the deformable guidewire shaft between the proximal and distal bonds is not coupled to the balloon. The deformable guidewire shaft defines a lumen in fluid communication with a guidewire lumen of the main catheter shaft and an inflation lumen of the main catheter shaft is in fluid communication with an interior of the balloon. The balloon catheter is percuataneously advanced through a vasculature to a target location. The balloon is inflated, and balloon inflation causes the balloon and the deformable guidewire shaft to bend in radially opposing directions, thereby orienting the distal end of the deformable guidewire shaft in a direction different from that of the main catheter shaft.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a catheter having a balloon and a deformable guidewire shaft according to an embodiment hereof, the balloon being proximally bonded to a main catheter shaft and distally bonded to the deformable guidewire shaft, wherein the balloon is in a delivery or deflated configuration.

FIG. 1A is a cross-sectional view taken along line A-A of FIG. 1.

FIG. 1B is a cross-sectional view taken along line A-A of FIG. 1 according to another embodiment hereof in which the main catheter shaft is formed via multi-lumen extrusion.

FIG. 3 is a side view of a distal portion of a catheter having a balloon and a deformable guidewire shaft according to another embodiment hereof, the deformable guidewire shaft being a coiled shaft, wherein the balloon is in a delivery or deflated configuration.

FIG. 4 is a side view of a distal portion of a catheter having a balloon and a deformable guidewire shaft according to another embodiment hereof, the catheter including a radiopaque marker within the balloon, wherein the balloon is in a deployed or inflated configuration.

FIG. 6 is a side view of a distal portion of a catheter having a balloon and a deformable guidewire shaft according to another embodiment hereof, wherein intermediate portions of the balloon and the deformable guidewire shaft may be selectively magnetically coupled together and the balloon is in a delivery or deflated configuration.

FIG. 6A is a side view of the catheter of FIG. 6, wherein intermediate portions of the balloon and the deformable guidewire shaft are selectively magnetically coupled and the balloon is in a deployed or inflated configuration.

FIG. 6B is a side view of the catheter of FIG. 6, wherein intermediate portions of the balloon and the deformable guidewire shaft are not magnetically coupled and the balloon is in a deployed or inflated configuration.

FIG. 7 is a side view of a distal portion of a catheter having a balloon and two deformable guidewire shafts according to another embodiment hereof, wherein the balloon is in a delivery or deflated configuration.

FIG. 7A is a cross-sectional view taken along line A-A of FIG. 7.

FIG. 7B is a side view of the catheter of FIG. 7, wherein the balloon is in a deployed or inflated configuration.

FIGS. 8A-8C illustrate a method of using the catheter of FIG. 6 at a bifurcation.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" is a position distant from or in a direction away from the clinician. "Proximal" or "proximally" is a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, and in general the peripheral vasculature (e.g. femoral and popliteal arteries), the invention may also be used in any other body passageways where it is deemed useful. Furthermore, there is no intention to be bound by any expressed or implied theory presented in the preceding technical field, background, brief summary or the following detailed description.

Embodiments hereof relate to a catheter having a distal balloon and a deformable guidewire shaft which is adjacent and external to the balloon. Inflation of the balloon deflects or bends the deformable guidewire shaft in order to orient or angle a distal end of the guidewire shaft in a desired direction to guide and direct a guidewire extending through the deformable guidewire shaft towards a specific endovascular region.

Figure 2:
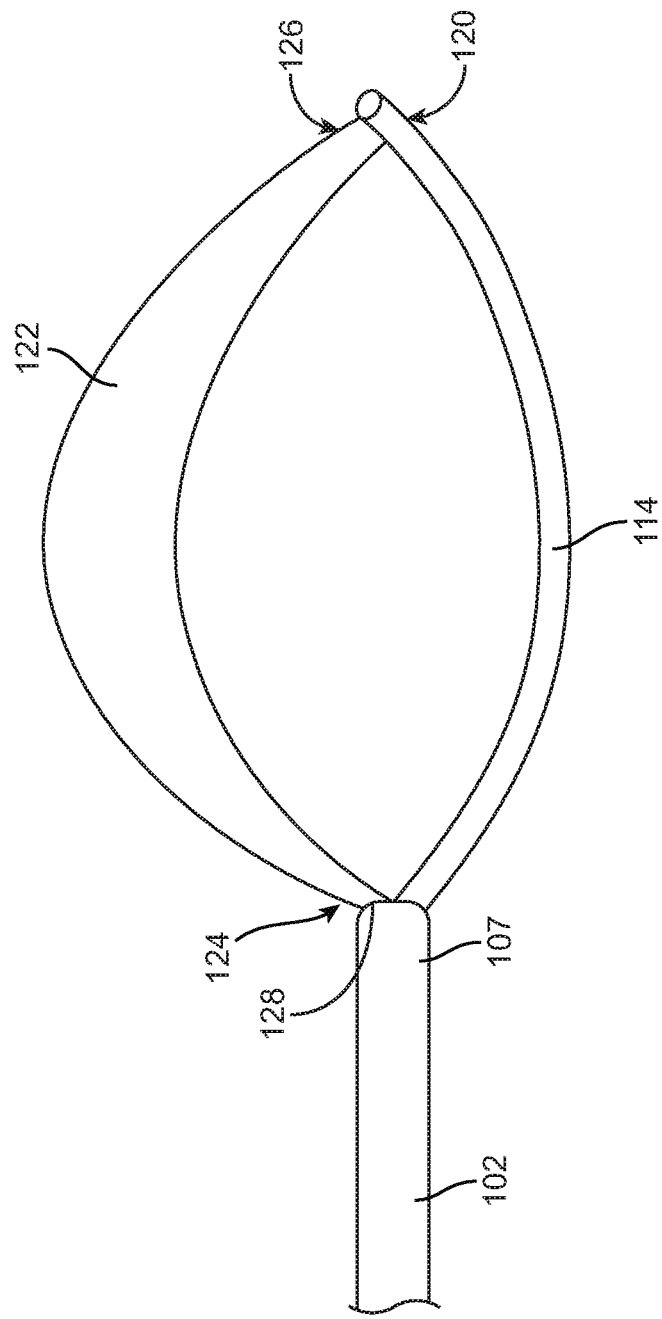
FIG. 2 is a side view of a distal portion of the catheter of FIG. 1, wherein the balloon is in a deployed or inflated configuration and balloon inflation causes a distal end of the deformable guidewire shaft to bend or deflect with respect to the main catheter shaft.

More particularly, with reference FIG. 1, FIG. 1A, and FIG. 2, a balloon catheter 100 includes a main or elongated catheter shaft 102 defining a lumen 104, an inflatable balloon 122, and a deformable guidewire shaft 114 defining a lumen 116 and being positioned adjacent and external to balloon 122. Deformable guidewire shaft 114 extends longitudinally along an exterior surface of balloon 122. Balloon 122 is shown in an unexpanded or delivery configuration in FIG. 1 and is shown in an expanded or inflated configuration in FIG. 2. In the catheter construction of the embodiment shown in FIGS. 1 and 1A, a guidewire shaft or tube 106 defining a lumen 108 and an inflation shaft or tube 110 defining an inflation lumen 112 extends through lumen 104 of main catheter shaft 102. Deformable guidewire shaft 114 is coupled to and extends from a distal end 107 of main catheter shaft 102 so that it forms a continuation or extension of guidewire shaft 106 and lumen 116 of deformable guidewire shaft 114 is in fluid communication with lumen 108 of guidewire shaft 106. As such, guidewire shaft 106 and deformable guidewire shaft 114 collectively define a guidewire lumen that extends substantially the entire length of the catheter for accommodating a guidewire (not shown in FIG. 1). Other types of catheter construction are also amendable to the invention, such as, without limitation thereto, a catheter shaft formed by multi-lumen profile extrusion as shown in FIG. 1B in which a main catheter shaft 102B is a dual lumen tubular component that includes an inflation lumen 112B and a guidewire lumen 108B. In another embodiment hereof (not shown), catheter 100 may be modified to be of a rapid exchange (RX) catheter configuration without departing from the scope of the present invention such that guidewire shaft 106 extends within only the distal portion of main catheter shaft 102.

Main catheter shaft 102 has a proximal end 118, which also defines a proximal end of catheter 100, which extends out of the patient and is coupled to a hub 103. Distal end 107 of main catheter shaft 102 is coupled to a proximal end or neck 124 of balloon 122. A distal end or neck 126 of balloon 122 is coupled to a distal end 120 of deformable guidewire shaft 114, which defines a distal guidewire port as well as a distal end of catheter 100. Distal end 120 may include a tapered distal catheter tip (not shown).

Inflation lumen 112 extends between proximal and distal ends 118, 107, respectively, of main catheter shaft 102 to allow inflation fluid received through hub 103 to be delivered to balloon 122. As would be understood by one of ordinary skill in the art of balloon catheter design, hub 103 provides a luer hub or other type of fitting that may be connected to a source of inflation fluid and may be of another construction or configuration without departing from the scope of the present invention.

The catheter shafts, including main catheter shaft 102, guidewire shaft 106, and inflation shaft 110, may be formed of a polymeric material, non-exhaustive examples of which include polyethylene, polyethylene block amide copolymer (PEBA), polyamide and/or combinations thereof, either laminated, blended or co-extruded. Optionally, main catheter shaft 102 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of main catheter shaft 102 may be formed from a reinforced polymeric tube.

Balloon 122 is fixed to catheter 100 via two constraints, a proximal bond 128 and a distal bond 130. An outer surface of deformable guidewire shaft 114 between the proximal and distal bonds is not bonded or otherwise coupled to balloon 122. Proximal bond 128 fixes or couples proximal end 124 of balloon 122 to main catheter shaft 102, and inflation lumen 112 of main catheter shaft 102 is in fluid communication with the interior of balloon 122. Distal bond 130 fixes or couples distal end 126 of balloon 122 to a distal end 120 of deformable guidewire shaft 114. The distance or length between proximal and distal bonds 128, 130, in which balloon 122 and deformable guidewire shaft 114 are not coupled together, is equal to or slightly less than the length of balloon 122 prior to inflation thereof. More particularly, in an embodiment, balloon 122 may have a length of 10-60 mm and the distance or length between proximal and distal bonds 128, 130 may be between 80 and 90% of the balloon length. The distance between proximal and distal bonds 128, 130 is a function of the amount of desired bending needed, i.e., a shorter distance results in less bending. Proximal and distal bonds 128, 130 may be formed in any conventional manner known to one of skill in the art of balloon catheter construction, such as by laser welding, adhesives, heat fusing, or ultrasonic welding.

Referring now to FIG. 2, inflation of balloon 122 causes balloon 122 and deformable guidewire shaft 114 to bend, curve, or bow in radially opposing directions, thereby orienting or deflecting distal end 120 of deformable guidewire shaft 114 in a direction different from that of the main catheter shaft 102. More particularly, prior to inflation or in a deflated state, both balloon 122 and deformable guidewire shaft 114 are straight and have a first longitudinal length. Balloon 122 is formed of a compliant or semi-compliant material and as balloon 122 inflates, pressure stretches the balloon walls in both the radial and longitudinal directions. As a result, as balloon 122 inflates, the longitudinal length of the balloon increases from the first longitudinal length to a second longitudinal length, which is greater than the first longitudinal length, and a diameter of the balloon increases from a first diameter to a second diameter. Such stretching is achieved due to the capability of polymer fibers of the balloon material to align and withstand inflation pressures. On the other hand, deformable guidewire shaft 114 maintains the same length and diameter, i.e., the length and diameter of deformable guidewire shaft 114 does not change during balloon inflation. Since proximal and distal ends 124, 126 of balloon 122 are constrained or fixed via proximal and distal bonds 128, 130, inflation of balloon 122 causes the balloon to bend or bow as the longitudinal length of the balloon increases from the first longitudinal length to the second longitudinal length. Meanwhile, in order to balance the forces developed during balloon inflation, deformable guidewire shaft 114 bends or bows with its concavity directed towards balloon 122. As a result, distal end 120 of deformable guidewire shaft 114 is oriented in a direction different from that of main shaft 102. Hence, as a function of the balloon inflation, during the procedure a guidewire which is inserted through the guidewire lumen can be oriented according to different directions, in particular different from the longitudinal straight direction collectively defined by guidewire shaft 106 and deformable guidewire shaft 114.

The amount of deflection or bending of deformable guidewire shaft 114 is dependent upon various factors including inflation pressure, balloon compliance, and material characteristics of deformable guidewire shaft 114. Most notably, the amount of deflection or bending of deformable guidewire shaft 114 is a function of inflation pressure. In general, the more balloon 122 is inflated, the greater amount of bending or deflection occurs or is produced in deformable guidewire shaft 114.

Compliance of balloon 122 also affects the amount of deflection or bending of deformable guidewire shaft 114. Balloon compliance can be defined as the change in balloon diameter and length as a function of inflation pressure. A high compliant balloon has a relatively large increase in diameter and length in response to an increase in inflation pressure, while a balloon having a relatively small increase in diameter and length in response to an increase in inflation pressure is said to be a low compliant balloon or a non-compliant balloon. In general, higher balloon compliance results in more deflection or bending of balloon 122, which in turn results in more deflection or bending of deformable guidewire shaft 114. As such, balloon 122 is formed from a compliant or semi-compliant material in order to result in the desired bending thereof. Non-exhaustive examples of materials for balloon 122 include polymers such as polyethylene, PEBA, polyethylene terephthalate (PET), polyamide, and polyurethane, copolymers or blends thereof. In one embodiment, balloon 122 is a relatively compliant thermoplastic elastomer (TPE) material. The size of balloon 122 will vary according to application. However, in an embodiment hereof, the second longitudinal length of balloon 122 in an inflated or expanded state is between 10 and 60 mm and the second diameter of balloon 122 in an inflated or expanded state is between 1 and 3 mm in order to minimize the size of the distal portion of catheter 100 when balloon 122 is inflated in situ.

In addition to material properties of balloon 122, material properties of deformable shaft extension 114 also affect the amount of deflection or bending of deformable guidewire shaft 114. The material and the mechanical characteristics of deformable guidewire shaft 114 are chosen to optimize the deformability or flexibility thereof. For this reason, deformable guidewire shaft 114 is a separate component from guidewire shaft 106 and has different material properties from guidewire shaft 106. A proximal end of deformable guidewire shaft 114 is coupled to a distal end of guidewire shaft 106 to form a continuous guidewire lumen as described above. However, in another embodiment hereof (not shown), guidewire shaft 114 and guidewire shaft 106 may be a continuous shaft or tube of the same material. In order to ensure that deformable guidewire shaft 114 bends in response to balloon inflation while main shaft 102 remain straight, deformable guidewire shaft 114 is constructed such that the bending stiffness $M_G$ thereof is lower than bending stiffness $M_M$ of main shaft 102. In an embodiment hereof, bending stiffness $M_G$ of deformable guidewire shaft 114 is approximately equal to or in the same range as the bending stiffness of balloon 122 in order to guarantee a sufficient bending rate while inflating the balloon. Bending stiffness may be defined as M=EJ, where E is the elastic modulus of the material and J is the cross section moment of inertia.

The target bending stiffness $M_G$ of deformable guidewire shaft 114 may be achieved either by means of a proper geometrical construction of deformable guidewire shaft 114 and/or by means of selecting a particular material for deformable guidewire shaft 114. With respect to the geometrical construction of deformable guidewire shaft 114, it is desirable to reduce or minimize the cross section moment of inertia by reducing or minimizing inner and outer diameters of deformable guidewire shaft 114 or, if deformable guidewire shaft 114 has a non-circular cross section, changing geometrical characteristics of the cross section of deformable guidewire shaft 114. However, the size of lumen 116 of deformable guidewire shaft 114 must remain of sufficient size to accommodate a guidewire.

With respect to selection of a particular material for deformable guidewire shaft 114, it is desirable to reduce or minimize the elastic modulus of the material. The elastic modulus of the material for deformable guidewire shaft 114 may vary between 0.01-10 GPa. Non-exhaustive examples of materials for deformable guidewire shaft 114 include a polyether block amide (PEBA) and a standard polyamide such as Nylon 12, Nylon 66. Selection of material for deformable guidewire shaft 114 may occur after balloon material and size are selected. For example, if a relatively small balloon is selected, e.g. a standard nylon balloon, 10 mm length, 1 mm nominal diameter, the expected amount of longitudinal compliance recovered during inflation is small and accordingly, material selection deformable guidewire shaft 114 would be a very soft material having a low elastic modulus.

In an embodiment hereof, shown in FIG. 3, a coil 340 may be wrapped around an outermost surface of deformable guidewire shaft 114 in order to enhance flexibility and allow for proper bending thereof without kinking. Pitch length and wire characteristics of coil 340 may be chosen or designed to increase bending performance. For example, coil 340 may be constructed with a ribbon or flat wire, or with a round wire, to increase bending performance thereof. A round wire having a circular cross section may reduce friction between adjacent windings of coil 340. Pitch or pitch length between windings of coil 340 may vary in a range of 0.005-0.05 inches. Pitch may be chosen or designed in order to provide the desired stiffness of coil. In general, a shorter pitch in which the windings of coil 340 are relatively close together results in increased stiffness. According to another embodiment hereof, rather than having a coil wrapped around deformable guidewire shaft 114, the deformable guidewire shaft itself may be a coil or may have a coil construction. For example, a coil may be co-extruded with a polymeric tube that forms or makes the deformable guidewire shaft.

It may be desirable to monitor the position of balloon 122 during inflation in order to determine whether additional inflation and bending thereof is required. Thus, in an embodiment shown in FIG. 4, catheter 100 may include a relatively small shaft or tube 442 having a radiopaque marker band 444 mounted on or adjacent to its distal end 446. A proximal end 448 of tube 442 is positioned within inflation lumen 112 of main shaft 102 and is fixed or coupled to an inside surface of inflation tube 110. Distal end 446, having marker band 444 thereon, extends distally and protrudes into balloon 122. Distal end 446 is not constrained or coupled to balloon 122, but an intermediate bond 450 may be included to couple tube 442 to a distal portion of main shaft 102 and/or a proximal portion of balloon 122. During balloon inflation, distal end 446 of tube 442 follows or moves with balloon 122, thus providing a visual indication of the position of balloon 122. In addition to marker 444, additional radiopaque markers (not shown) may be placed on main shaft 102 and/or deformable guidewire shaft 114. Additional radiopaque markers allow visibility of position/orientation of the balloon with respect to the position/orientation of the main shaft and/or deformable guidewire shaft. Further, according to another embodiment (not shown), tube 442 may be omitted and inflation tube 110 may extend into and within balloon 122, distal to proximal bond 128, and a radiopaque marker band may be mounted adjacent to a distal end of inflation tube 110.

Figure 5:
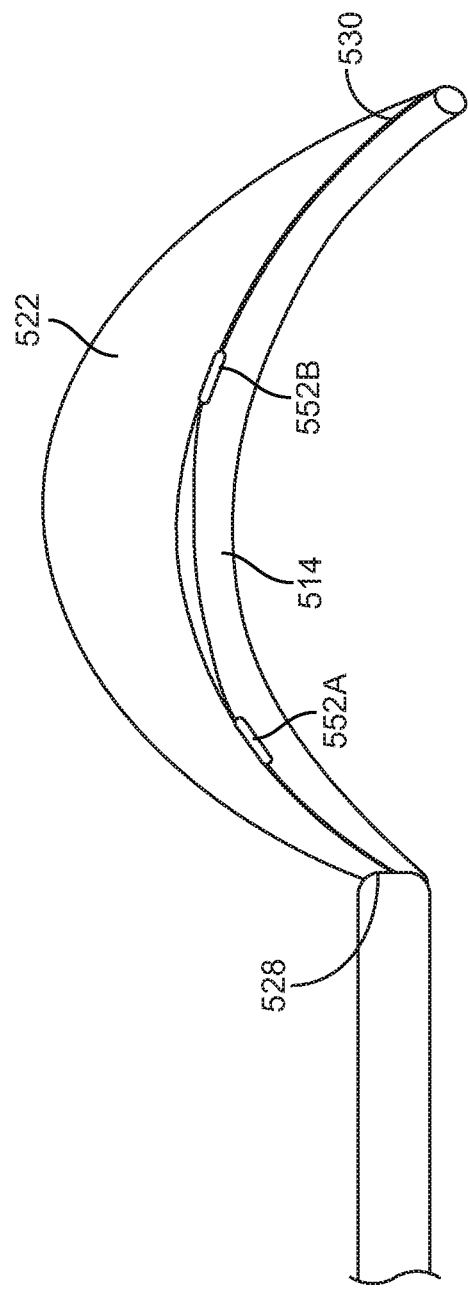
FIG. 5 is a side view of a distal portion of a catheter having a balloon and a deformable guidewire shaft according to another embodiment hereof, the catheter including additional bonds between intermediate portions of the balloon and the deformable guidewire shaft, wherein the balloon is in a deployed or inflated configuration.

During some procedures, it may be desirable for the balloon and the deformable guidewire shaft to bend, curve, or bow in the same radial direction rather than radially opposing directions as described with respect to FIG. 2. Referring to FIG. 5, another embodiment hereof is shown in which two additional bonds 552A, 552B are provided between a balloon 522 and a deformable guidewire shaft 514 which force the deformable guidewire shaft to bend in the same direction as the balloon. Additional bonds 552A, 55B are positioned between proximal and distal bonds 528, 530, which have placement and function similar to proximal and distal bonds 128, 130 described above. Although FIG. 5 illustrates two additional bonds to couple an intermediate or middle portion of deformable guidewire shaft 514 to an intermediate or middle portion of balloon 522, a greater or less number of additional bonds may be used. Since the intermediate or middle portion of deformable guidewire shaft 514 remains connected or coupled to balloon 522 through additional constraints, i.e., bonds 552A, 552B, deformable guidewire shaft 514 starts bending with its concavity directed in the same direction as the concavity of the balloon. Additional bonds 552A, 55B may be formed in any conventional manner known to one of skill in the art of balloon catheter construction, such as by laser welding, adhesives, heat fusing, or ultrasonic welding.

According to further embodiments hereof, a balloon catheter includes a deformable guidewire shaft that has the capability to bend in the same direction as the balloon and/or in a radially opposing direction as the balloon. The bending direction may be selectively decided in situ by the operator. More particularly, a balloon catheter 600 is shown in FIG. 6. Similar to balloon catheter 100, balloon catheter 600 includes a main catheter shaft 602 having a guidewire lumen (not shown) and an inflation lumen (not shown), a deformable guidewire shaft 614, and a balloon 622. Deformable guidewire shaft 614 extends from a distal end 607 of main catheter shaft 602, adjacent and external to balloon 622, and the deformable guidewire shaft defines a lumen in fluid communication with the guidewire lumen of the main catheter shaft. Balloon 622 extends from distal end 607 of main catheter shaft 602, and the inflation lumen of the main catheter shaft is in fluid communication with an interior of the balloon. Also similar to balloon catheter 100, a proximal bond 628 fixes a proximal end of the balloon to distal end 607 of main catheter shaft 602 and a distal bond 630 fixes a distal end of balloon 622 to a distal end 620 of deformable guidewire shaft 614. An outer surface of deformable guidewire shaft 614 between proximal bond 628 and the distal bond 630 is not bonded to balloon 622.

The bending direction of deformable guidewire shaft 614 may be selectively decided in situ by the operator via first and second magnetic components 660, 662. First magnetic component 660 is coupled/bonded to or insertable within or over an intermediate portion of balloon 622, and second magnetic component 662 is coupled to or insertable within or over an intermediate portion of deformable guidewire shaft 614. The first and second magnetic components are operable to selectively and temporarily couple the intermediate portion of balloon 622 and the intermediate portion of deformable guidewire shaft 614 together. Coupling between balloon 622 and deformable guidewire shaft 614 is selectively achieved by means of the magnetic force between first and second magnetic components 660, 662. When the intermediate portions of the balloon and deformable guidewire shaft are coupled together and balloon 622 is inflated, first and second magnetic components 660, 662 operate or function similar to additional bonds 552A, 552B described with respect to FIG. 5 and cause deformable guidewire shaft 614 to bend in the same direction as balloon 622 as shown in FIG. 6A. However, as shown in FIG. 6B, when the intermediate portions of the balloon and deformable guidewire shaft are not coupled together and balloon 622 is inflated, balloon 622 and deformable guidewire shaft 614 bend in radially opposing directions as described with respect to FIG. 2.

In a first embodiment, in order to provide catheter 600 and deformable guidewire shaft 614 with the capability of selectively bending in one of two opposing directions, first magnetic component 660 is coupled to a distal end of an elongate component 664 that is slidingly insertable within the inflation lumen of catheter 600 in order to position first magnetic component 660 at an intermediate portion of balloon 622. Second magnetic component 662 is coupled to an inner or outer surface of deformable shaft component 614. Alternatively, in another embodiment (not shown), first magnetic component 660 may be coupled to a surface of balloon 622 or may be coupled to an interior tube that extends into balloon 622, such as tube 442 described with respect to FIG. 4, and second magnetic component 662 may be selectively insertable into deformable shaft component 614. Both first and second magnetic components 660, 662 may be formed from a magnetic material, or one of first and second magnetic components 660, 662 is formed from a magnetic material and the other is formed from a ferromagnetic material.

In a second embodiment, in order to provide catheter 600 and deformable guidewire shaft 614 with the capability of selectively bending in one of two opposing directions, first magnetic component 660 is an electromagnet while second magnetic component 662 is formed from a ferromagnetic material. An electromagnet is a type of magnet in which a magnetic field is produced by the flow of electric current. When the current is turned on, the electromagnet creates a magnetic field and when the current is turned off, the electromagnet does not create a magnetic field. As such, coupling between the intermediate portions of the balloon and deformable guidewire shaft can be selectively activated by turning the electric current flowing into the electromagnet on or off. In this embodiment, an elongated conductor 666 such as a wire extends through the inflation lumen of catheter 600 and connects the electromagnetic, which is magnetic components 660, to an external current generator (not shown) which is located external to the catheter. Alternatively, in another embodiment (not shown), second magnetic component 662 is the electromagnet and first magnetic component 660 is formed from a ferromagnetic material.

FIG. 7 illustrates another embodiment hereof in which a balloon catheter 700 includes two deformable guidewire shafts which bend in opposing directions so that the direction of a guidewire inserted there through may be selectively decided in situ by the operator. Balloon catheter 700 includes a main catheter shaft 702, a first deformable guidewire shaft 714A, a second deformable guidewire shaft 714B, and a balloon 722. As shown in FIG. 7A, main catheter shaft 702 includes a first guidewire lumen 706A, a second guidewire lumen 706B, and an inflation lumen 712. First deformable guidewire shaft 714A extends from a distal end 707 of main catheter shaft 702, adjacent and external to balloon 722, and the first deformable guidewire shaft defines a lumen 716A in fluid communication with first guidewire lumen 706A of main catheter shaft 702. Second deformable guidewire shaft 714B also extends from distal end 707 of main catheter shaft 702, adjacent and external to balloon 722, and the second deformable guidewire shaft defines a lumen 716B in fluid communication with second guidewire lumen 706B of main catheter shaft 702. Balloon 722 also extends from distal end 707 of the main catheter shaft, and inflation lumen 712 of main catheter shaft 702 is in fluid communication with an interior of balloon 722.

Essentially, first deformable guidewire shaft 714A is coupled to balloon 722 in the same manner as guidewire shaft 114 described with respect to FIGS. 1-2, while second deformable guidewire shaft 714B is coupled to balloon in the same manner as guidewire shaft 514 described with respect to FIG. 5. More particularly, a proximal bond 728 fixes a proximal end of balloon 722 to distal end 707 of main catheter shaft 702. First distal bond 730A fixes a distal end of balloon 722 to distal end 720A of first deformable guidewire shaft 714A, and second distal bond 730B fixes distal end 720A of first deformable guidewire shaft 714A to distal end 720B of second deformable guidewire shaft 714B, thereby coupling the distal ends of balloon 722 and first and second deformable guidewire shafts 714A, 714B together. In another embodiment hereof (not shown), the distal end of balloon 722 may be coupled to each distal end 720A, 720B, of first and second deformable guidewire shafts 714A, 714B, respectively. Regardless of the particular construction, the distal ends of balloon 722 and first and second deformable guidewire shafts 714A, 714B are coupled or bonded together. An outer surface of first deformable guidewire shaft 714A between proximal bond 728 and first distal bond 730A is not bonded to the balloon, while at least one intermediate bond 752 fixes an intermediate portion of balloon 722 to an intermediate portion of second deformable guidewire shaft 714B. Similar to deformable guidewire shaft 114, balloon inflation causes balloon 722 and first deformable guidewire shaft 714A to bend in radially opposing directions while, similar to deformable guidewire shaft 514 having additional intermediary constraints, balloon inflation causes balloon 722 and second deformable guidewire shaft 714B to bend in the same direction. Distal ends 720A, 720B of first and second deformable guidewire shafts 714A, 714B are thus oriented in different directions, thereby providing two different options or directions to the operator to direct a guidewire inserted through catheter 700. A guidewire may be inserted through guidewire lumen 706A and lumen 716A, or may alternatively be inserted through guidewire lumen 706B and lumen 716B, thereby obtaining two different opposite directions for the guidewire exiting from catheter 700.

Catheters having a construction which provide an operator with more than one guidewire direction, such as catheter 600 or catheter 700, are useful in applications such as a bifurcation or a chronic total occlusion (CTO). In order to orient a distal end of a balloon catheter in situ, the balloon catheter is percuataneously advanced through a vasculature to a target location. The balloon is inflated, and balloon inflation causes the balloon to bend in the first radial direction. The shaft component selectively bends in either the first radial direction with the balloon or a second opposing radial direction away from the balloon, thereby selectively orienting the distal end of the shaft component in a direction different from that of the main catheter shaft. More particularly, a method of using catheter 600 at a bifurcation is shown in FIGS. 8A-8C and a method of using catheter 600 to bypass a CTO is shown in FIGS. 9A-9F. Although the methods are illustrated with catheter 600, it will be understood by those of ordinary skill in the art that the methods may alternatively utilize catheter 100 or catheter 700 to direct the catheter distal end in particular direction.

Referring to FIG. 8A, catheter 600 is shown within the vasculature at a bifurcation having a main vessel MV, a first branch vessel $BV_1$, and a second branch vessel $BV_2$. The position of catheter 600 within the vasculature and the position of balloon 622 with respect to main shaft 602 are visible via radiopaque markers (not shown) on catheter 600. If it is desired to direct distal end 620 of catheter 600 towards second branch vessel $BV_2$, as shown in FIG. 8B, first and second magnetic components 660, 662 of balloon 622 and deformable guidewire shaft 614, respectively, are not magnetically coupled together. When balloon 622 is inflated as shown in FIG. 8B, balloon 622 and deformable guidewire shaft 614 bend in radially opposing directions as described with respect to FIG. 6B. As such, in FIG. 8B, guidewire 860 is shown inserted through catheter 600 and extending into second branch vessel $BV_2$. If it is desired to direct distal end 620 of catheter 600 towards first branch vessel $BV_1$, as shown in FIG. 8C, first and second magnetic components 660, 662 of balloon 622 and deformable guidewire shaft 614, respectively, are magnetically coupled together. When balloon 622 is inflated as shown in FIG. 8C, deformable guidewire shaft 614 bends in the same radial direction as balloon 622 as described with respect to FIG. 6A. As such, in FIG. 8C, guidewire 860 is shown inserted through catheter 600 and extending into first branch vessel $BV_1$. Thus, the bending direction of deformable guidewire shaft 614 may be selectively decided in situ by the operator, respectively magnetically coupling or decoupling first and second magnetic components 660, 662, in order to direct the distal end of the catheter towards a particular branch of the bifurcation, i.e., first branch vessel $BV_1$ and a second branch vessel $BV_2$.

Figure 9A:
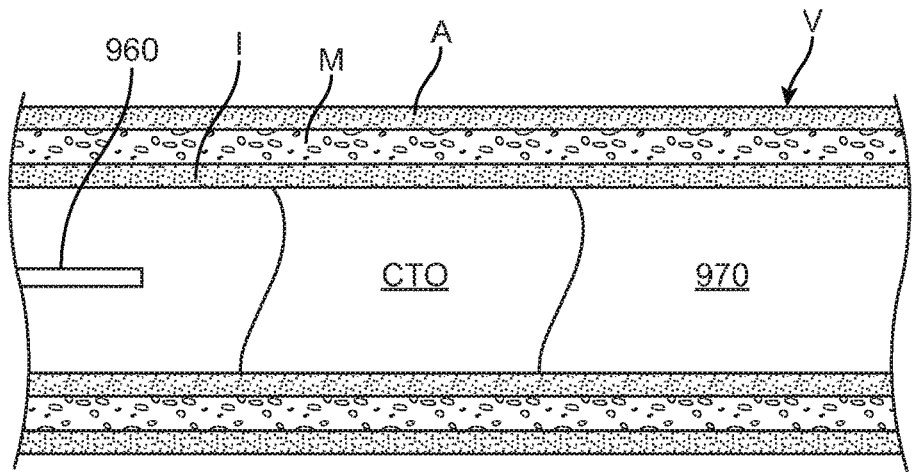
FIGS. 9A-9F illustrate a method of using the catheter of FIG. 6 to bypass a chronic total occlusion (CTO).

Referring to FIG. 9A, a guidewire 960 is shown at a portion upstream of a treatment site, which in this instance is a chronic total occlusion CTO within a lumen 970 of blood vessel V. For purposes of this description, the anatomy of vessel V includes essentially three layers, the tunica intima I ("intima"), tunica media M ("media") which is the thickest layer of the wall, and the tunica adventitia A ("adventitia"). In some arteries an internal elastic membrane is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. In some cases, such as where blood vessel is totally occluded by hard, calcified atherosclerotic plaque, a determinative factor of whether the operator can successfully recannalize the CTO is the operator's ability to advance a guidewire from a position within the true lumen of the main vessel proximal to the CTO lesion, across the CTO lesion, i.e., either through the lesion or around it, and then back into the true lumen of the main vessel at a location distal to the CTO lesion. One approach of crossing a CTO includes creating a neo-lumen called a "subintimal tract" i.e., a penetration tract formed within the wall of the artery between the intima and adventitia. In such instances, after crossing the CTO within the subintimal tract, it is necessary to divert or steer the guidewire from the subintimal tract back into the true lumen of the blood vessel at a location distal to the CTO lesion. Although described in relation to bypassing a CTO, it should be understood that the methods and apparatus described herein may be used for bypassing any tight stenoses in arteries or other anatomical conduits and are not limited to total occlusions.

Figure 9B:
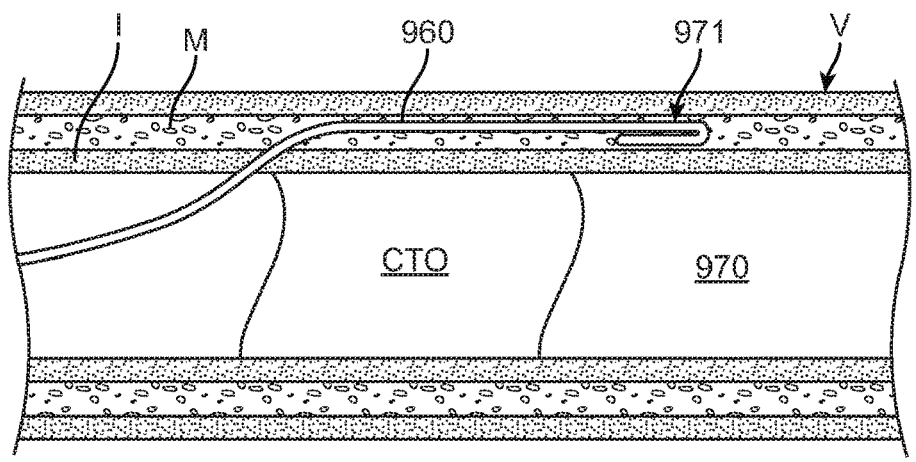

Referring to FIG. 9B, in accordance with techniques known in the field of interventional cardiology and/or interventional radiology, a distal end of guidewire 960 pierces the intima I and is advanced distally to create a subintimal tract by locally dissecting or delaminating intima I from media M or by burrowing through media M. In order to pierce the intima I, a clinician may manipulate the distal end of guidewire 960 by prolapsing or bending-over the distal end thereof to create a stiffer arc or loop 971 that is operable to pierce into the intima I as shown in FIG. 9B. The piercing of the intima I is aided by the fact that typically blood vessel V is diseased, which in some instances makes the intima I prone to piercing. Alternatively, another device other than guidewire 960 inserted through catheter 600 may be initially used to create the subintimal tract. Those of ordinary skill in the art will appreciate and understand the types of alternative devices that may be used in this step including an apparatus known as an "olive", a laser wire, an elongate radiofrequency electrode, or any other device suitable for boring or advancing through the vessel tissue. If an alternative device is used instead of guidewire 960 to form the subintimal tract, such alternative device may be removed and replaced with guidewire 960 after the subintimal tract has been formed.

Figure 9C:
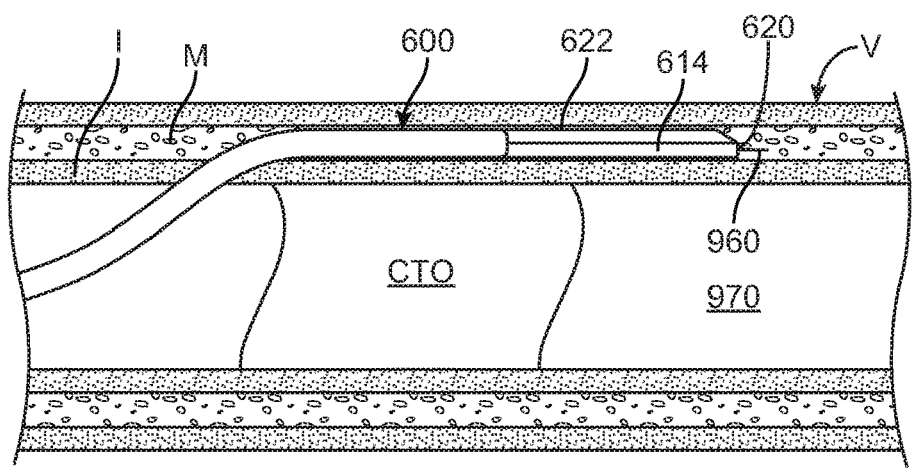

Catheter 600 is transluminally advanced over guidewire 960 and within the subintimal tract from a near side of the CTO to a position where distal end 620 of catheter 600 is positioned in the subintimal tract on a far side of the CTO, as shown in FIG. 9C. Guidewire 960 is partially withdrawn until its distal end only slightly extends from distal end 620 of catheter 600, or until its distal end is positioned flush with the distal end 620 of catheter 600. If one or more optional radiopaque markers are present which indicate the position of balloon 622 with respect to main shaft 602, they may be used by the operator to ensure that catheter 600 is oriented as desired with respect to true lumen 970 with deformable guidewire shaft 614 adjacent or next to the true lumen.

Figure 9D:
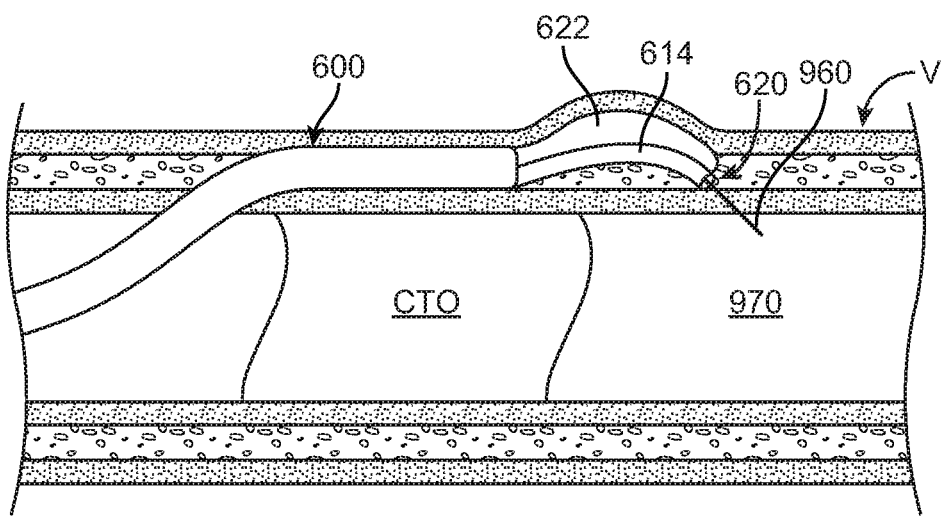

Once catheter 600 is positioned within the subintimal tract with distal end 620 downstream of the CTO as desired, first and second magnetic components 660, 662 (not shown on FIGS. 9A-9F) of balloon 622 and deformable guidewire shaft 614, respectively, are magnetically coupled together. Once the catheter is positioned and oriented to re-enter the true lumen, balloon 622 is inflated as shown in FIG. 9D. Since deformable guidewire shaft 614 is magnetically coupled to the balloon, deformable guidewire shaft 614 bends in the same radial direction as balloon 622 as described with respect to FIG. 6A. If the catheter is disposed in a reverse direction with balloon 622 being positioned between deformable guidewire shaft 614 and true lumen 970, first and second magnetic components 660, 662 may be decoupled such that deformable guidewire shaft 614 bends in an opposite radial direction than balloon 622 when balloon 622 is inflated. Thus, advantageously, since first and second magnetic components 660, 662 may be coupled or decoupled in situ, the operator may select or chose which radial direction to bend deformable guidewire shaft 614 on the basis of how the catheter is positioned and oriented in the subintimal space at the target site. The catheter orientation determines how to operate first and second magnetic components 660, 662 to have deformable guidewire shaft 614 and balloon 622 bend in the same direction or in radially opposing directions. When distal end 620 is bent or deformed to the desired extent towards lumen 970 of blood vessel V, guidewire 960 is pushed through the intima and into the true lumen of the blood vessel distal to, i.e., downstream of, the CTO. Guidewire 960 extends in true lumen 970 proximal to the CTO, through the subintimal tract, and back into true lumen 970 distal to the CTO such that the CTO may now be successfully crossed via the subintimal conduit thus created.

Figure 9E:
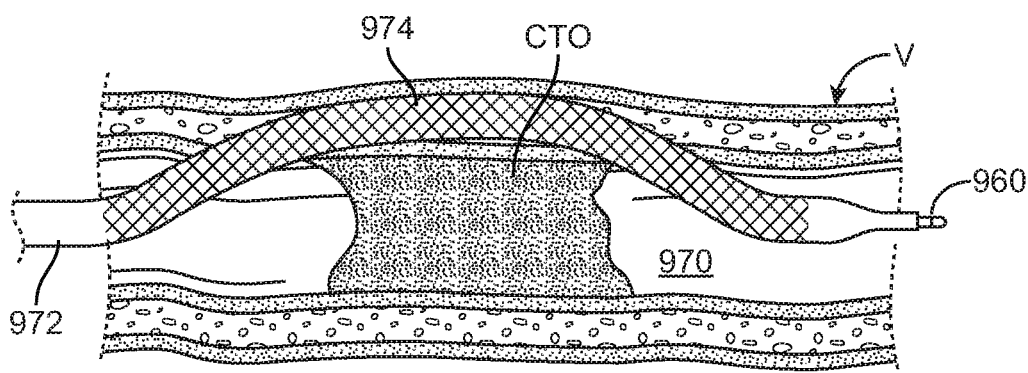
Figure 9F:
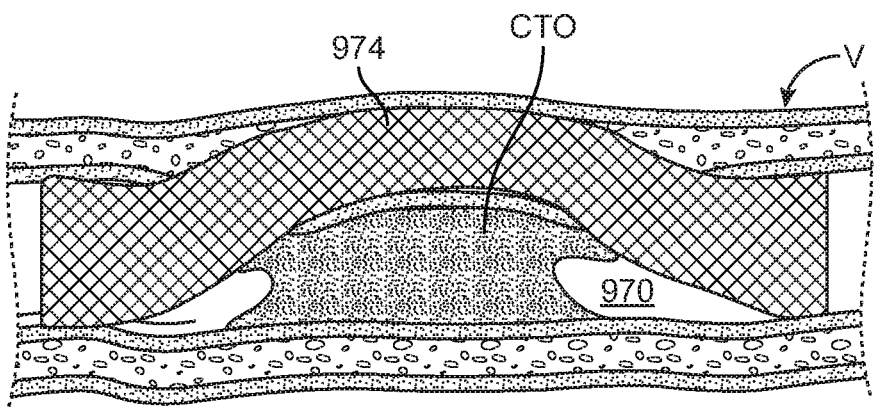

Optionally, balloon catheter 600 may be removed and a covered or uncovered stent may be delivered and implanted within the subintimal reentry conduit to facilitate flow from the lumen of the vessel upstream of the CTO, through the subintimal tract and back into the lumen of the vessel downstream of the CTO. For example, FIG. 9E shows a distal end of a catheter 972 having a stent 974 mounted thereon being advanced over guidewire 960 to a position where a distal end of the radially collapsed stent 974 is in true lumen 970 of vessel V downstream of chronic total occlusion CTO, a proximal end of stent 974 is in true lumen 970 of vessel V upstream of chronic total occlusion CTO, and a mid-portion of stent 974 extends through the subintimal reentry conduit. Stent 974 is then deployed by either self-expansion or balloon inflation within the subintimal reentry conduit to dilate the subintimal reentry conduit and compress the adjacent chronic total occlusion CTO. Stent 974 provides a scaffold which maintains the subintimal reentry conduit in an open condition capable of carrying blood downstream of chronic total occlusion CTO. Thereafter, guidewire 960 and catheter 972 may be removed from the patient, leaving stent 974 in an expanded configuration and creating a radially supported, subintimal blood flow channel around chronic total occlusion CTO as seen in FIG. 9F. In some cases, it may be desirable to enlarge the diameter of the subintimal tract before advancing stent catheter 972 into and through it. Such enlargement of the subintimal tract may be accomplished by passing a balloon catheter over guidewire 960 and inflating the balloon to dilate the tract, or may be any other suitable tract enlarging, dilating or de-bulking instrument that may be passed over guidewire 960.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A balloon catheter comprising:
   a main catheter shaft including a first guidewire lumen, a second guidewire lumen, and an inflation lumen;
   a balloon extending from a distal end of the main catheter shaft, wherein the inflation lumen of the main catheter shaft is in fluid communication with an interior of the balloon;
   a first deformable guidewire shaft extending from the distal end of the main catheter shaft, adjacent and external to the balloon, wherein the first deformable guidewire shaft defines a lumen in fluid communication with the first guidewire lumen of the main catheter shaft;
   a second deformable guidewire shaft extending from the distal end of the main catheter shaft, adjacent and external to the balloon, wherein the second deformable guidewire shaft defines a lumen in fluid communication with the second guidewire lumen of the main catheter shaft;
   a proximal bond that fixes a proximal end of the balloon to the distal end of the main catheter shaft;
   a first distal bond that fixes a distal end of the balloon to the first distal end of the first deformable guidewire shaft or a second distal end of the second deformable guidewire shaft, and a second distal bond that fixes the first distal end of the first deformable guidewire shaft to the second distal end of the second deformable guidewire shaft;
   at least one intermediate bond that fixes an intermediate portion of the balloon to an intermediate portion of the second deformable guidewire shaft, wherein an outer surface of the first deformable guidewire shaft between the proximal bond and the first distal bond is not bonded to the balloon and is not bonded to the second deformable guidewire shaft, and
   wherein balloon inflation causes the balloon and the first deformable guidewire shaft to bend in radially opposing directions and causes the balloon and the second deformable guidewire shaft to bend in the same direction, thereby orienting the distal ends of the first and second deformable guidewire shafts in directions different from that of the main catheter shaft.

2. The balloon catheter of claim 1, wherein a distance between the proximal bond and the first distal bond is equal to a length of the balloon prior to inflation thereof.

3. The balloon catheter of claim 1, wherein the first guidewire lumen of the main catheter shaft, the second guidewire lumen of the main catheter shaft, and the inflation lumen are formed by multi-lumen profile extrusion.

4. The balloon catheter of claim 1, wherein the first guidewire lumen is defined by a guidewire shaft that extends through the main catheter shaft and the inflation lumen is defined by an inflation shaft that extends through the main catheter shaft and wherein a proximal end of the first deformable guidewire shaft is coupled to a distal end of the guidewire shaft defining the first guidewire lumen.

5. The balloon catheter of claim 4, wherein the first deformable guidewire shaft includes a coil.

6. The balloon catheter of claim 4, wherein the first deformable guidewire shaft has a lower bending stiffness than the main catheter shaft such that the main catheter shaft remains straight during bending of the first deformable guidewire shaft.

7. The balloon catheter of claim 6, wherein the bending stiffness of the first deformable guidewire shaft is equal to the bending stiffness of the balloon.

8. The balloon catheter of claim 1, further comprising a tubular component which extends through at least a portion of the inflation lumen and includes a distal end that extends into the interior of the balloon, wherein a radiopaque marker band is mounted on the distal end of the tubular component.

9. The balloon catheter of claim 1, wherein the second guidewire lumen is defined by a guidewire shaft that extends through the main catheter shaft and the inflation lumen is defined by an inflation shaft that extends through the main catheter shaft and wherein a proximal end of the second deformable guidewire shaft is coupled to a distal end of the guidewire shaft defining the second guidewire lumen.

10. The balloon catheter of claim 9, wherein the second deformable guidewire shaft includes a coil.

11. The balloon catheter of claim 9, wherein the second deformable guidewire shaft has a lower bending stiffness than the main catheter shaft such that the main catheter shaft remains straight during bending of the second deformable guidewire shaft.

12. The balloon catheter of claim 11, wherein the bending stiffness of the second deformable guidewire shaft is equal to the bending stiffness of the balloon.

* * * * *